US00PP24207P2

(12) United States Plant Patent
Kordes

(10) Patent No.: US PP24,207 P2
(45) Date of Patent: Feb. 4, 2014

(54) MINIATURE ROSE PLANT NAMED 'KORPOT021'

(50) Latin Name: *Rosa hybrida*
Varietal Denomination: KORpot021

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 85 days.

(21) Appl. No.: 13/385,826

(22) Filed: Mar. 7, 2012

(51) Int. Cl.
*A01H 5/00* (2006.01)

(52) U.S. Cl.
USPC ..... Plt./119; Plt./101; Plt./116

(58) Field of Classification Search
USPC ..... Plt./101, 116, 119, 120
See application file for complete search history.

*Primary Examiner* — Susan McCormick Ewoldt

(57) ABSTRACT

A new and distinct variety of rose with long lasting, novel apricot-orange flowers, and attractive foliage with very good disease resistance. It exhibits an upright to bushy habit, as well as moderately vigorous growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot021'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2008. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot021'.

SUMMARY OF THE INVENTION

The new rose plant may be distinguished from its seed parent, an 'un-named seedling', by the following combination of characteristics:

1. 'KORpot021' has very double apricot-orange flowers, whereas the seed parent has semi-double yellow-apricot flowers.
2. 'KORpot021' has a high centered flower shape, whereas the seed parent has a cupped flower shape.

The new rose plant may be distinguished from its pollen parent, an 'un-named seedling', by the following combination of characteristics:

1. 'KORpot021' has large, elegant flowers, whereas the pollen parent has medium, roundish flowers.

2. 'KORpot021' has a tall growth habit, whereas the pollen parent has a medium growth habit.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot021' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot021' was selected in May, 2009 from the seedling beds to be asexually propagated for further evaluation. The first asexual propagation of 'KORpot021' was done by cutting propagation in August, 2009 at the inventor's nursery in Offenseth-Sparrieshoop, Germany.

This initial and other subsequent propagations conducted in controlled environments demonstrate that 'KORpot021' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot021'.

DETAILED BOTANICAL DESCRIPTION

The following is a description of 'KORpot021', as observed growing in January, 2012 in a nursery in Jackson County, Oreg. on plants 4 months of age. Color references are made using The Royal Horticultural Society (London, England) Colour Chart, 2001 except where common terms of color are used.

For a comparison, several physical characteristics of the rose variety 'KORbailand', a rose variety from the same inventor filed as patent application Ser. No. 13/065,651 on Mar. 25, 2011, are compared to 'KORpot021' in Chart 1.

CHART 1

| Characteristic | 'KORpot021' | 'KORbailand' |
|---|---|---|
| Fragrance | Light-moderate, floral | None |
| General Tonality | Orange-Red Group 32D | Red Group 40D |
| Petal Count | 45-60 | 25-35 |

Parents:

*Seed parent*.—'Un-named seedling'.

*Pollen parent*.—'Un-named seedling'.

Classification:

*Botanical classification*.—*Rosa hybrida* 'KORpot021'.

*Commercial classification*.—Miniature rose.

FLOWER AND FLOWER BUD

Blooming habit: Recurrent.

Flower bud:

*Size*.—Upon opening, 28-32 mm in length from base of receptacle to distal end of bud and 50-60 mm in diameter at its widest point.

*Bud form*.—Long, pointed ovoid.

*Bud color*.—As sepals first unfold, bud color is Red Group 39A and Red Group 37B. When ¼ open, the upper surface of petals is Red Group 39C, and the lower surface is Red Group 39B. Guard Petals are Red Group 38C with intonations of Red Group 40D and Yellow-Green Group 146D.

*Sepals*.—Color: Upper surface Green Group 137B. Lower surface Green Group 137A. Intonations of Greyed-Purple Group 187A were seen at distal ends of some sepals. Size: Average 28-30 mm (l)×7-8 mm (w). Shape: Moderate foliaceous appendages on 3 of the 5 sepals. Apex: Apiculate. Base: Flat at union with receptacle. Quantity: Five. Surface texture: Upper side: Pubescent. Lower surface: Smooth with occasional stipitate glands. Margins: Pubescent with limited numbers of stipitate glands.

Receptacle:

*Surface*.—Smooth.

*Color*.—Yellow-Green Group 144B.

*Shape*.—Funnel.

*Size*.—8-10 mm (h)×8-10 mm (w).

Peduncle:

*Surface*.—Generally smooth with fine hairs and occasional stipitate glands.

*Length*.—32 to 36 mm average length.

*Diameter*.—8 to 10 mm average diameter.

*Color*.—Yellow-Green Group 144B.

*Strength*.—Strong.

*Borne*.—Singularly.

Flower bloom:

*Fragrance*.—Light-moderate floral fragrance.

*Duration*.—On the plant 10 to 14 days. Long lasting. Senesced petals clinging.

*Size*.—Medium to large for a miniature rose. When open, the average flower diameter is 50-55 mm and the average flower height is 30-34 mm.

*Form*.—Shape of flower when viewed from the side: Upon opening, upper part: Flat. Upon opening, lower part: Flat. Open flower, upper part: Flattened convex. Open flower, lower part: Flattened convex.

Color:

*Upon opening, petals*.—Outermost petals: Outer Side: Red Group 39B with intonations of Orange Group 26B on margins. Inner Side: Red Group 43D. Innermost petals: Outer Side: Orange-Red Group 32C and Orange-Red Group 32D. Inner Side: Orange-Red Group 32D.

*Upon opening, basal petal spots*.—Basal petal spot, outermost petals: Outer Side: Orange-Red Group 32C. Inner Side: Orange-Red Group 32B. Basal petal spot, innermost petals: Outer Side: Green-Yellow Group 1C. Inner Side: Yellow Group 2B.

*After opening, petals*.—Outermost petals: Outer Side: Red Group 39B. Inner Side: Red Group 39C. Innermost petals: Outer Side: Orange Group 28C with a marginal zone of Yellow-Orange Group 23B. Inner Side: Orange-Red Group 32C with a marginal zone of Yellow-Orange Group 22C.

*After opening, basal petal spots*.—Basal petal spot, outermost petals: Outer Side: Green-Yellow Group 1C. Inner Side: Yellow Group 2A. Basal petal spot, innermost petals: Outer Side: Yellow Group 2A. Inner Side Green-Yellow Group 1A.

General tonality: On open flower Orange-Red Group 32D. No change in the general tonality at the end of the $7^{th}$-$8^{th}$ day. Afterwards, general tonality is Orange Group 29C to Orange Group 29D.

Petals:

*Petal count*.—Very double.

*Average range*.—Approximately 45 to 60 petals under normal conditions.

*Petal reflex*.—Petals reflex somewhat strongly, a moderate single petal reflex.

*Petal edge*.—Entire, with a point in the center.

*Petal shape*.—Oval. Apex shape is retuse. Shape of base is obtuse.

*Petal size*.—Outer petals: 25 mm (l)×25 mm (w). Inner petals: 20 mm (l)×15 mm (w).

*Thickness*.—Average.

*Petal arrangement*.—Not formal.

Petaloids:

*Petaloid count*.—Average of 12 to 15 per flower.

*Petaloid size*.—Petaloids are 5-10 mm (l) and 10-15 mm (w).

*Petaloid color*.—Color of inner side is Orange Group 25C in the basal zone and Yellow-Orange Group 23B in the marginal zone. Color of outer side is the same.

*Petaloid texture*.—Smooth.

*Margins*.—Smooth, undulated, indented, and irregular.

*Petaloid shape*.—Most commonly oblanceolate, with some petaloids highly irregular. Often crinkled or folded. Many petaloids are not complete, with edges cut out. Apex: Acute. Base: Attenuate.

Reproductive organs:

*Pistils*.—Approximately 20 to 30 present. Stigmas: Location: Slightly superior in position to anthers. Color: Green-Yellow Group 1C. Styles: Length: About 10 mm long. Color: Green-Yellow Group 1C.

*Stamens*.—Approximately 30 on average and regularly arranged. Anthers: Size: Average 2 mm (l)×1 mm (w). Pollen: Generally absent. Color: Green-Yellow Group 1D. Filaments: Color: Yellow Group 2A. Length: 3-4 mm.

THE PLANT

*Growth*.—Moderately vigorous.

*Plant habit*.—Upright to bushy habit. When grown as a 10.5 cm pot plant, the average plant height is 25-30 cm and the average plant width is 15-20 cm.

*Blooming*.—Floriferous.

*Stems*.—Stem color: Young wood: Yellow-Green Group 144A. Older wood: Yellow-Green Group 144A. Stem surface: Young wood: Smooth. Older wood: Smooth.

*Prickles*.—Present. Incidence: Average of 2 to 3 per each 10 cm of stem. Size: Average length: 2-3 mm. Color: Immature prickles: Greyed-Green Group 195B to Greyed-Green Group 195C. Mature prickles: Brown Group 200C. Shape: Linear.

*Leaves and leaflets*.—Normally 5 leaflets on normal leaves in middle of the stem. Venation pattern: Pyramidal net pattern. Leaf size: 50-60 mm (l)×50 mm (w). Abundance: Average. Texture: Thin. Upper side of leaflet: Semi-glossy. Under side of leaflet: Matte. Color, mature foliage: Upper Leaf Surface: Green Group 136A. Lower Leaf Surface: Green Group 137B. Color, juvenile foliage: Upper Leaf Surface: Green Group 136A. Lower Leaf Surface: Green Group 137C. Anthocyanin intonation: Present. Intonations of Greyed-Purple Group 187A present on juvenile leaves, especially when grown at cooler temperatures.

*Stipules*.—Size: 10-12 mm long, 5 mm from distal tip to distal tip. Stipule color: Green Group 137A. Anthocyanin: Greyed-Purple Group 184B on tips and center rib. Stipitate glands: Limited on margins. Shape: Apex: Apiculate. Base: Slightly winged.

*Petiole*.—Length: Average 12-15 mm. Diameter: Average 1-1.5 mm. Petiole color: Yellow-Green Group 146A. Underneath: Yellow-Green Group 146B. Margins: With stipitate glands. Anthocyanin: Greyed-Purple Group 184A on immature foliage. Prickles: Present underneath. Stipitate Glands: Abundant on margins.

*Petiole rachis*.—Length: Average 10-11 mm. Diameter: Average 1 mm. Color: Yellow-Green Group 146B. Anthocyanin present on juvenile tissue: Greyed-Purple Group 184B. Margins: With stipitate glands. Prickles: A few small prickles underneath.

*Leaflets*.—Size: Average size of the terminal leaflet is 35-40 mm (l)×15-20 mm (w). Shape: Obovate. Base: Obtuse. Apex: Acute. Margins: Finely serrated . Surface: Upper: Moderately glossy. Lower: Matte finish. Texture: Smooth. Arrangement: Odd pinnate Venation: Reticulate.

Hips/seed formation: Not observed.

Winter hardiness: Unknown.

Disease resistance: Very good resistance to Powdery mildew (*Sphaerotheca pannosa*) and Botrytis (*Botrytis cinerea*) diseases under normal growing conditions.

I claim:

1. A new and distinct variety of rose plant, as described and illustrated herein.

* * * * *

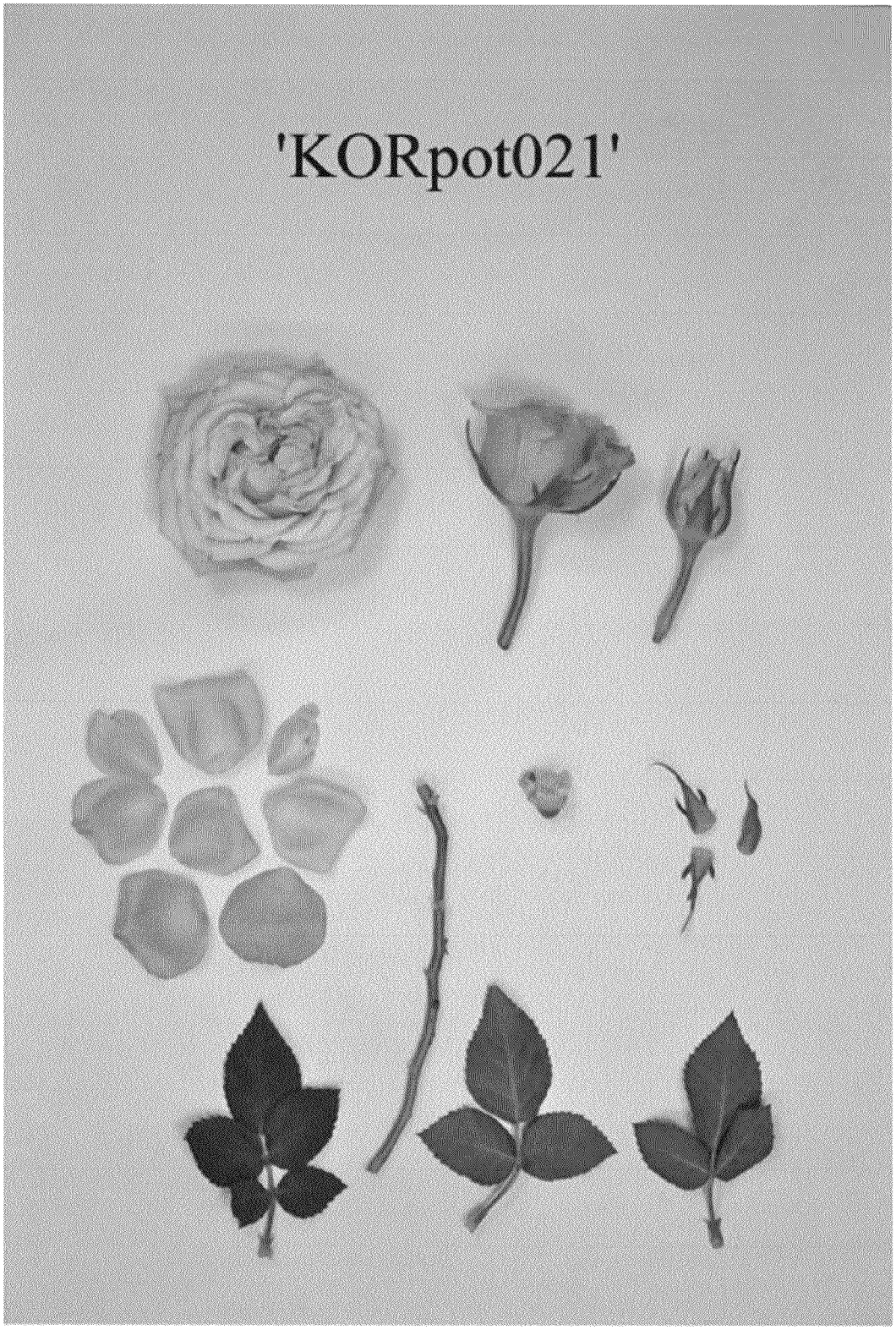
'KORpot021'